US009095315B2

(12) United States Patent
Arazi

(10) Patent No.: US 9,095,315 B2
(45) Date of Patent: Aug. 4, 2015

(54) METHOD AND APPARATUS INTEGRATING CLINICAL DATA WITH THE REVIEW OF MEDICAL IMAGES

(71) Applicant: McKesson Financial Holdings, Hamilton (BM)

(72) Inventor: Ohad Arazi, Vancouver (CA)

(73) Assignee: McKesson Financial Holdings, Hamilton (BM)

( * ) Notice: Subject to any disclaimer, the term of this patent is extended or adjusted under 35 U.S.C. 154(b) by 86 days.

(21) Appl. No.: 13/836,666

(22) Filed: Mar. 15, 2013

(65) Prior Publication Data

US 2014/0140591 A1     May 22, 2014

Related U.S. Application Data

(60) Provisional application No. 61/729,183, filed on Nov. 21, 2012.

(51) Int. Cl.
| | |
|---|---|
| *G06K 9/00* | (2006.01) |
| *A61B 5/00* | (2006.01) |
| *G06F 19/00* | (2011.01) |
| *A61B 6/00* | (2006.01) |

(52) U.S. Cl.
CPC ............ *A61B 5/7275* (2013.01); *G06F 19/321* (2013.01); *G06F 19/3431* (2013.01); *A61B 5/743* (2013.01); *A61B 5/744* (2013.01); *A61B 5/7425* (2013.01); *A61B 6/00* (2013.01)

(58) Field of Classification Search
USPC .................................................. 382/128–134
See application file for complete search history.

(56) References Cited

U.S. PATENT DOCUMENTS

| | | | | |
|---|---|---|---|---|
| 5,807,256 | A * | 9/1998 | Taguchi et al. ............... | 600/425 |
| 7,200,858 | B1 * | 4/2007 | Benjamin et al. ............ | 725/90 |
| 2003/0072477 | A1 * | 4/2003 | Kotwaliwale ................. | 382/129 |
| 2003/0095147 | A1 * | 5/2003 | Daw .............................. | 345/771 |
| 2003/0229278 | A1 * | 12/2003 | Sinha ............................ | 600/407 |
| 2004/0013292 | A1 * | 1/2004 | Raunig ......................... | 382/128 |
| 2005/0245803 | A1 * | 11/2005 | Glenn, Jr. et al. ............ | 600/407 |
| 2006/0159325 | A1 * | 7/2006 | Zeineh et al. ................ | 382/128 |
| 2007/0237375 | A1 * | 10/2007 | Yamagishi et al. .......... | 382/128 |
| 2008/0117230 | A1 * | 5/2008 | Wegenkittl et al. .......... | 345/619 |
| 2008/0123917 | A1 * | 5/2008 | Magsig et al. ............... | 382/128 |
| 2008/0184168 | A1 * | 7/2008 | Oda .............................. | 715/838 |
| 2009/0150184 | A1 * | 6/2009 | Spahn ............................ | 705/3 |
| 2010/0114608 | A1 * | 5/2010 | Ando ............................. | 705/3 |
| 2010/0142774 | A1 * | 6/2010 | Ben-Haim et al. ........... | 382/128 |
| 2011/0225530 | A1 * | 9/2011 | Osmundson et al. ........ | 715/771 |
| 2012/0253845 | A1 * | 10/2012 | Bocirnea ......................... | 705/3 |
| 2012/0254794 | A1 * | 10/2012 | Bocirnea ...................... | 715/809 |
| 2013/0152020 | A1 * | 6/2013 | Nishiyama ................... | 715/835 |
| 2013/0326386 | A1 * | 12/2013 | Vendrell ....................... | 715/771 |
| 2014/0143710 | A1 * | 5/2014 | Zhao et al. ................... | 715/781 |

* cited by examiner

*Primary Examiner* — Alex Liew
(74) *Attorney, Agent, or Firm* — Alston & Bird LLP

(57) ABSTRACT

A method, apparatus and computer program product are provided in order to integrate clinical data with the medical images reviewed by radiologists or other healthcare providers. In the context of a method, one or more findings related to a respective risk profile of a patient are identified. The method also includes concurrently presenting both one or more medical images of the patient and a visual representation of at least a portion of the patient's body with respect to visual indications of the one or more findings. The method also includes providing information regarding a respective finding upon selection of the visual indication associated with the respective finding. A corresponding apparatus and computer program product are also provided.

17 Claims, 4 Drawing Sheets

METHOD AND APPARATUS INTEGRATING CLINICAL DATA WITH THE REVIEW OF MEDICAL IMAGES

CROSS-REFERENCE TO RELATED APPLICATIONS

The present application claims priority from U.S. Provisional Patent Application No. 61/729,183 filed Nov. 21, 2012, the contents of which are incorporated herein in their entirety.

TECHNOLOGICAL FIELD

An example embodiment of the present invention relates generally to the presentation and review of medical images and, more particularly, to the concurrent presentation of both medical images of a patient and a visual representation of clinical data of the patient.

BACKGROUND

Medical imaging often includes creating images of regions of the human body for clinical purposes such as examination, diagnosis and/or treatment. These images may be acquired by a number of different imaging modalities including, for example, ultrasound (US), magnetic resonance (MR), positron emission tomography (PET), computed tomography (CT), mammograms (MG), digital radiology (DR), computed radiology (CR) or the like. In a number of example medical imaging workflows, such as in the case of a picture archiving and communication system (PACS), an image study for a patient may include one or more acquired images of the patient. A radiologist or other health care provider may review the images for diagnostic or other purposes.

In addition to medical images, a wide variety of other clinical data may be associated with a patient. Typically, the other clinical data associated with the patient has not been provided to the radiologist reviewing the medical images and, instead, the radiologist just received an order requisition. In this regard, the clinical data was generally handwritten or otherwise documented in hard copy and was not readily accessible to a radiologist.

Recently, electronic medical records have maintained clinical data in a digital form, but electronic medical records are not generally structured in a manner that is convenient for radiologists who are reviewing the medical images of a patient to review in parallel with the interpretation or protocoling of a patient's medical images. In this regard, an electronic medical record, including an electronic health summary report, often fails to include information that may be pertinent to the interpretation of the patient's medical images and/or presents the data in a text-based summary, which would require the radiologist who is reviewing the medical images of the patient to divert their attention from the medical images and to take time to parse and read the text-based summary. Additionally, data from an electronic medical record, if available, may be presented by another system, outside of the PACS, so as to further distract the radiologist from the review of the patient's medical images.

By way of example, the Caradigm Amalga system permits diagnostic users, such as radiologists, to correlate medical images with clinical data. The Caradigm Amalga system may permit a patient's white blood cell count to be presented along with all PET CT medical images, but not to show the patient's hemoglobin levels in conjunction with x-rays of the patient's knee. However, the Caradigm Amalga system presents clinical data in a text-based syntax-driven report in a system outside of the PACS, thereby creating inefficiencies for the radiologist who is studying the medical images of the patient and must divert their attention from the PACS in order to review the text-based report.

BRIEF SUMMARY

A method, apparatus and computer program product are provided in accordance with one embodiment of the present invention in order to integrate clinical data with the medical images reviewed by radiologists or other healthcare providers. In particular, the method, apparatus, and computer program product of an example embodiment may provide information regarding one or more findings related to a respective risk profile of a patient, which may inform the interpretation of the medical images. The method, apparatus and computer program product of an example embodiment may provide the clinical data in a manner that is easy to interpret and, in one embodiment, is presented by a PACS, thereby allowing a radiologist or other healthcare provider who is reviewing the medical images to consider the clinical data without diverting their attention from the review of the medical images. As such, the method, apparatus and computer program product of an example embodiment may improve the efficiency with which medical images are reviewed.

In one embodiment, a method is provided that includes identifying, with processing circuitry, one or more findings related to a respective risk profile of a patient. The method of this embodiment also includes concurrently presenting both one or more medical images of the patient and a visual representation of at least a portion of the patient's body with respect to visual indications of the one or more findings. In this embodiment, the method also includes providing information regarding a respective finding upon selection of the visual indication associated with the respective finding.

In another embodiment, an apparatus is provided that includes processing circuitry configured to identify one or more findings related to a respective risk profile of a patient. The processing circuitry of this embodiment is also configured to concurrently present both one or more medical images of the patient and a visual representation of at least a portion of the patient's body with respect to visual indications of the one or more findings. The processing circuitry is further configured in accordance with this embodiment to provide information regarding a respective finding upon selection of the visual indication associated with the respective finding.

In a further embodiment, a computer program product is provided that includes at least one non-transitory computer-readable storage medium having computer-executable program code instructions stored therein. The computer-executable program code instructions include program code instructions configured to identify one or more findings related to a respective risk profile of a patient. The computer-executable program code instructions of this embodiment also include program code instructions configured to concurrently present both one or more medical images of the patient and a visual representation of at least a portion of the patient's body with respect to visual indications of the one or more findings. The computer-executable program code instructions of this embodiment also include program code instructions configured to provide information regarding a respective finding upon selection of the visual indication associated with the respective finding.

In yet another embodiment, an apparatus is provided that includes means for identifying one or more findings related to a respective risk profile of a patient. The apparatus of this embodiment also includes means for concurrently presenting both one or more medical images of the patient and a visual representation of at least a portion of the patient's body with respective visual indications of the one or more findings. In this embodiment, the apparatus also includes means for providing information regarding a respective finding upon selection of the visual indication associated with the respective finding.

BRIEF DESCRIPTION OF THE DRAWINGS

Figure 1:
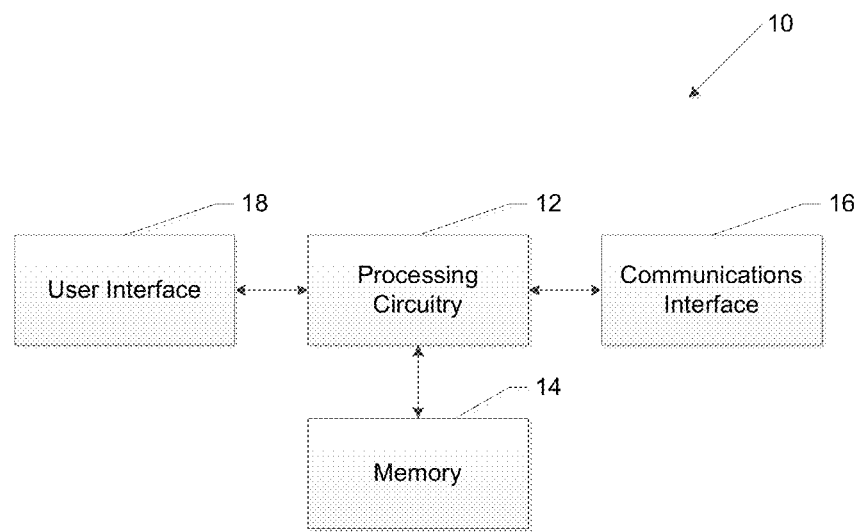
Figure 2:
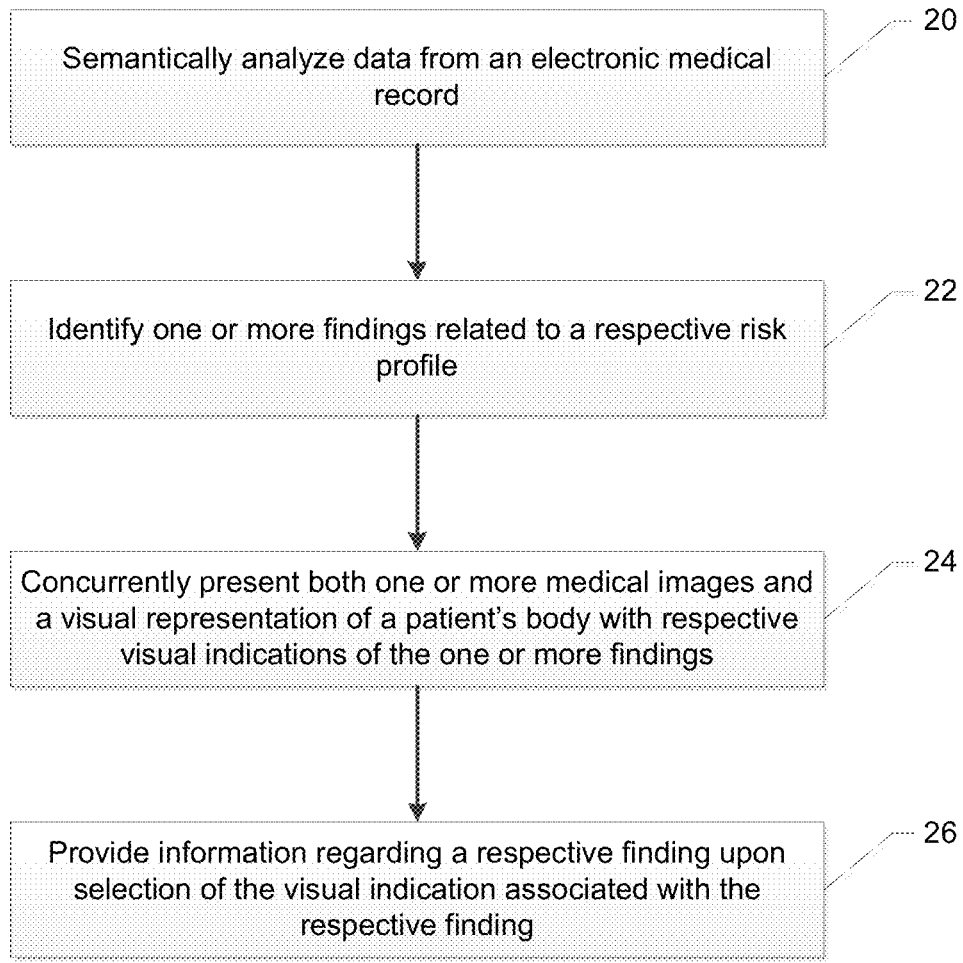
Figure 3:
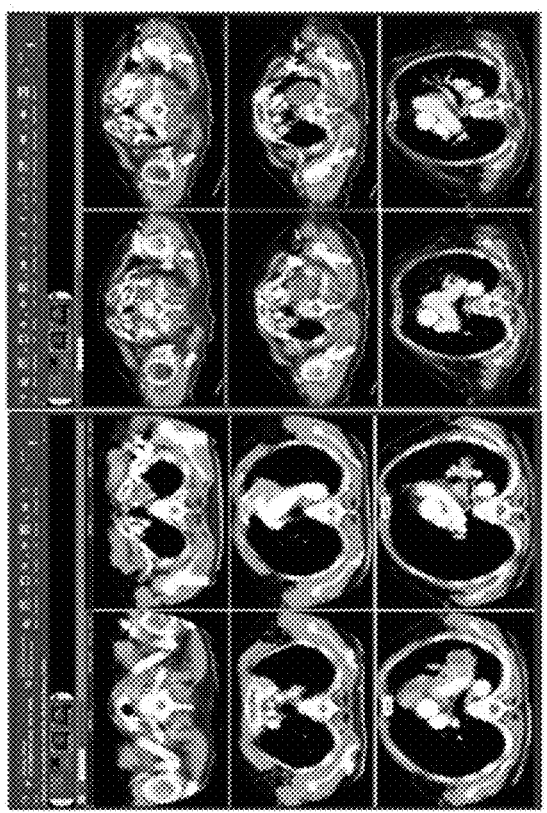
Figure 3:
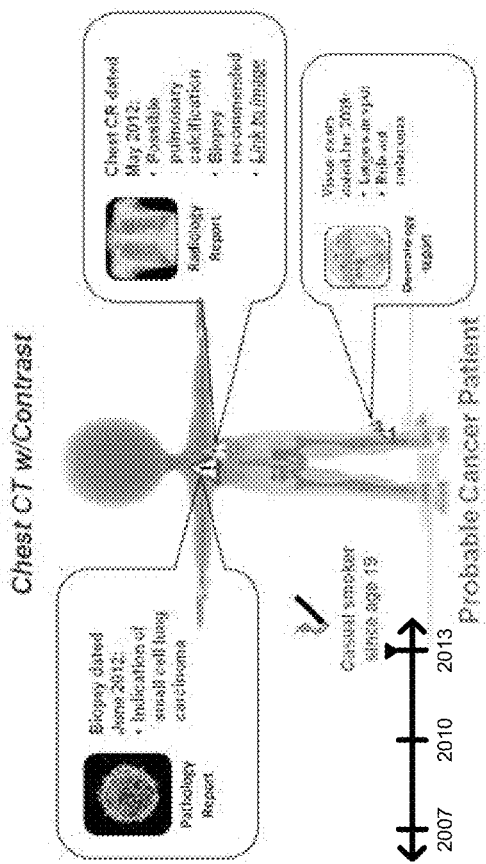
Figure 4:
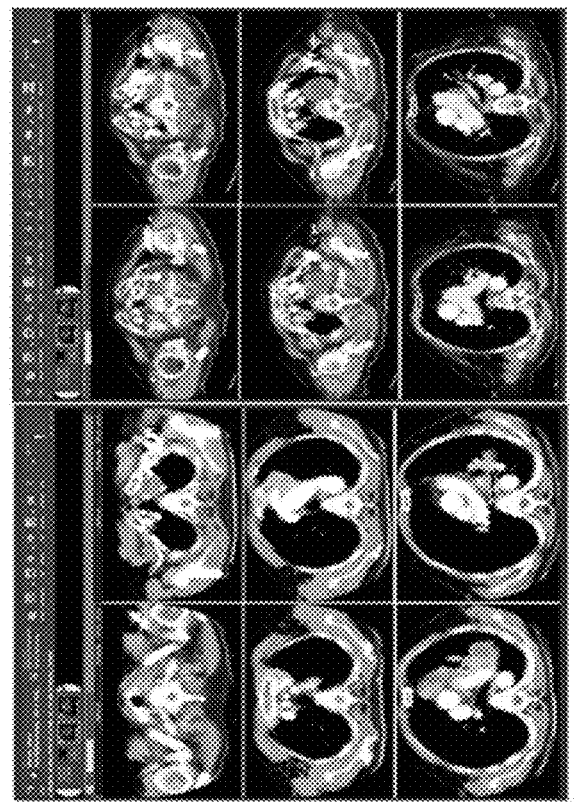
Figure 4:
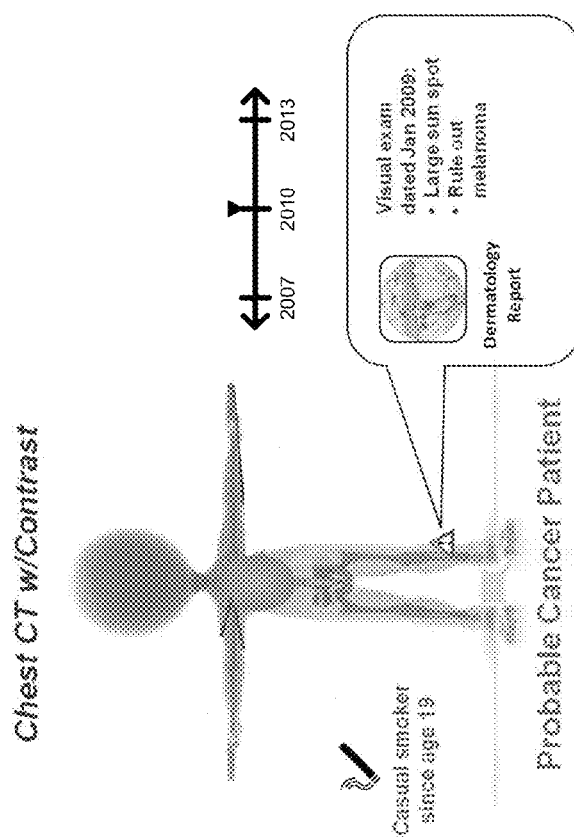

Having thus described embodiments of the invention in general terms, reference will now be made to the accompanying drawings, which are not necessarily drawn to scale, and wherein:

FIG. 1 is a block diagram of an apparatus that may be specifically configured in accordance with an example embodiment of the present invention;

FIG. 2 is a flow chart illustrating operations performed, such as by the apparatus of FIG. 1, in accordance with an example embodiment of the present invention;

FIG. 3 is an example of the concurrent presentation of a plurality of medical images of a patient and a visual representation of the patient's body with respective visual indications of a plurality of findings related to a respective risk profile of the patient in accordance with an example embodiment of the present invention; and FIG. 4 is another example of the concurrent presentation of a plurality of medical images of a patient and a visual representation of the patient's body from a prior point in time with a visual indication of a finding related to a dermatology report of the patient in accordance with an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

A method, apparatus and computer program product are provided in accordance with an example embodiment of the present invention in order to provide clinical data to a radiologist or other healthcare provider (hereinafter generically referred to as a "radiologist") who is reviewing one or more medical images of a patient in order to facilitate the review of the medical images or the establishment of a protocol associated with the review of the medical images. In this regard, the clinical data may include one or more findings related to a respective risk profile of a patient. As such, the clinical data that is provided to the radiologist who is reviewing the medical images of the patient may be of particular relevance in regards to the interpretation or protocoling of the medical images, thereby potentially improving the review of the medical images and/or increasing the efficiency with which those medical images are reviewed. Additionally, the method, apparatus and computer program product of an example embodiment of the present invention may provide the clinical data in a manner that is intuitive and readily reviewable by a radiologist who is reviewing the medical images and, in one embodiment, may be provided in such a manner that the radiologist need not divert their attention from the diagnostic imaging system, such as the PACS.

The method, apparatus and computer program product of an example embodiment of the present invention may be embodied by a computing device. In one embodiment, a diagnostic imaging system, such as a PACS, includes or is otherwise associated with the computing device that embodies the method, apparatus and computer program product of an example embodiment of the present invention. However, other types of computing devices may embody the method, apparatus and computer program product of an embodiment of the present invention.

Regardless of the instantiation of the computing device, the computing device may include or otherwise be associated with an apparatus 10 that may, in turn, be specifically configured in order to perform one or more operations in associated with an embodiment of the present invention. As shown in FIG. 1, for example, the apparatus of one embodiment may include various means for performing the various functions described herein. These means may include, for example, one or more of a processing circuitry 12, memory 14, communication interface 16 and/or user interface 18 for performing the various functions herein described. The means of the apparatus as described herein may be embodied as, for example, circuitry, hardware elements (e.g., a suitably programmed processor, combinational logic circuit, and/or the like), a computer program product comprising computer-readable program instructions (e.g., software or firmware) stored on a computer-readable medium (e.g. memory) that is executable by a suitably configured processing device (e.g., the processing circuitry), or some combination thereof.

The processing circuitry 12 may, for example, be embodied as various means including one or more microprocessors, one or more coprocessors, one or more multi-core processors, one or more controllers, one or more computers, various other processing elements including integrated circuits such as, for example, an ASIC (application specific integrated circuit) or FPGA (field programmable gate array), or some combination thereof. Accordingly, although illustrated in FIG. 1 as a single processing circuitry, in some embodiments the processor may comprise a plurality of processing circuits. The plurality of processing circuits may be embodied on a single computing device or may be distributed across a plurality of computing devices collectively configured to function as the apparatus. The plurality of processing circuits may be in operative communication with each other and may be collectively configured to perform one or more functionalities of the apparatus as described herein. In some example embodiments, the processing circuitry is configured to execute instructions stored in the memory 14 or otherwise accessible to the processing circuitry. These instructions, when executed by the processing circuitry, may cause the apparatus 10 to perform one or more of the functionalities of the apparatus as described herein. As such, whether configured by hardware or software methods, or by a combination thereof, the processing circuitry may comprise an entity capable of performing operations according to embodiments of the present invention while configured accordingly. Thus, for example, when the processing circuitry is embodied as an ASIC, FPGA or the like, the processing circuitry may comprise specifically configured hardware for conducting one or more operations described herein. Alternatively, as another example, when the processing circuitry is embodied as an executor of instructions, such as may be stored in the memory, the instructions may specifically configure the processing circuitry to perform one or more algorithms and operations described herein.

The memory 14 may include, for example, volatile and/or non-volatile memory. Although illustrated in FIG. 1 as a single memory, the memory may comprise a plurality of memories. The plurality of memories may be embodied on a single computing device or distributed across a plurality of computing devices. The memory may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory may comprise any non-transitory computer readable storage medium. The memory may be configured to store information, data, applications, instructions, or the like for enabling the apparatus 10 to carry out various functions in accordance with example embodiments of the present invention. For example, in some example embodiments, the memory is configured to buffer input data for processing by the processing circuitry 12. Additionally or alternatively, in some example embodiments, the memory is configured to store program instructions for execution by the processing device.

The communication interface 16 may be embodied as any device or means embodied in circuitry, hardware, a computer program product comprising computer readable program instructions stored on a computer readable medium (e.g., the memory 14) and executed by the processing circuitry 12, or a combination thereof that is configured to receive and/or transmit data from/to another device, such as, for example, a data storage device or other archive for storing electronic medical records. In some example embodiments, the communication interface is at least partially embodied as or otherwise controlled by the processing circuitry. In this regard, the communication interface may be in communication with the processing circuitry, such as via a bus. The communication interface may provide for communications via a wireline connection or may support wireless communications in which the communication interface may include, for example, an antenna, a transmitter, a receiver, a transceiver and/or supporting hardware or software for enabling communications. The communication interface may be configured to receive and/or transmit data using any protocol that may be used for communications between computing devices. As an example, the communication interface may be configured to receive and/or transmit data using any protocol and/or communications technology that may be used for communicating with the other devices. The communication interface may additionally be in communication with the memory and/or user interface 18, such as via a bus.

The user interface 18 may be in communication with the processing circuitry 12 to receive an indication of a user input and/or to provide an audible, visual, mechanical, or other output to a user. As such, the user interface may include, for example, a keyboard, a mouse, a joystick, a display, a touch screen display, a microphone, a speaker, and/or other input/output mechanisms. The user interface may be in communication with the memory 14 and/or communication interface 16, such as via a bus.

Referring now of FIG. 2, the operations performed, such as by the apparatus 10 of FIG. 1, in accordance with an example embodiment of the present invention are illustrated. In this regard, the apparatus may include means, such as the processing circuit 12, for identifying one or more findings related to a respective risk profile of a patient. See block 22. In this regard, various risk profiles may be established. For example, a first risk profile may be the profile of a patient who is at risk of having cancer, a second risk profile may be the profile of a patient who is at risk of having HIV and a third risk profile may be the profile of a patient who is at risk of having diabetes. As noted, a variety of risk profiles may be predefined with each risk profile being helpful to a radiologist who is reviewing the medical images of a patient in regards to the interpretation or protocoling of the medical images. In other words, knowledge of a risk profile of a patient may facilitate the review of the medical images by the radiologist, thereby providing for a more accurate and/or efficient review of the medical images. Not only are the plurality of risk profiles predefined, but the subset of risk profiles that are relevant for a particular type of medical image may also be predefined, thereby tailoring the review and presentation of the clinical data based upon the type of imaging study to be conducted.

In conjunction with the review of the medical images of a particular patient, the method, apparatus and computer program product may determine if the clinical data associated with the patient is related to, is associated with or otherwise supports any one or more of the respective risk profiles, such as the risk profile(s) that are predefined to be relevant for a particular type of medical image. In this regard, the apparatus 10 may include means, such as a processing circuitry 12, for reviewing the clinical data associated with the patient, such as by reviewing the electronic medical record of the patient, and identifying one or more findings related to a respective risk profile of the patient. The review of the data from an electronic medical record may include the review of metadata which may facilitate the classification of the data. The apparatus, such as the processing circuitry, may review the clinical data, such as the electronic medical record, associated with a patient in various manners. In one embodiment, however, the apparatus may include means, such as the processing circuitry, for semantically analyzing data from the electronic medical record of the patient and, based upon the semantic analysis, identifying one or more findings related to the respective risk profile of the patient. See block 20 of FIG. 2.

As noted above, the plurality of risk profiles may be predefined. Further, the findings that will be considered to be related to a respective risk profile, a type of medical image and/or a purpose of the study may also be predefined in order to facilitate the review of the clinical data, such as the semantic analysis of data from the electronic medical record, in conjunction with the identification of one or more findings related to the respective risk profile. By way of example, in conjunction with a magnetic resonance image (MRI) that is conducted to determine if a patient has prostate cancer, data from the electronic medical record that relates to known histories of breast cancer within the patient's family may be disregarded. However, data regarding a familial history of breast cancer may be considered as a relevant finding with respect to a cancer risk profile in regards to the interpretation of mammograms.

As shown in block 24 of FIG. 2, the apparatus 10 may also include means, such as the processing circuitry 12, the user interface 18 or the like, for concurrently presenting both one or more medical images and a visual representation of the patient's body with respective visual indications of the one or more findings. In one embodiment, the medical images may be presented upon the display screen(s) of the PACS and the visual representation of the patient's body with respective visual indications of the findings related to respective risk profiles may be presented either upon the same display screen(s) or upon an auxiliary screen of the PACS, thereby facilitating the review of both the medical images and the visual representation of the patient's body without diverting the attention of the radiologist who is reviewing the medical images from the PACS. However, the medical images and the visual representation of the patient's body with respective visual indications of the one or more findings may be presented in other manners in conjunction with other embodiments. By providing a visual representation of the patient's body with respective visual indications of the one or more findings related to a respective risk profile of the patient, the findings may be presented in a manner that is intuitive and may be quickly reviewed by a radiologist who is reviewing the medical images so as not to divert the attention of the radiologist from the review of the medical images, while still providing relevant information in regards to the interpretation of protocoling of the medical images.

By way of example, FIG. 3 depicts the concurrent presentation of a plurality of medical images as well as a visual representation of the patient's body with visual indications of a plurality of findings related to a cancer risk profile. In regards to the display of FIG. 3, an example workflow of a radiologist may involve the radiologist initially accessing a previously un-read thoracic CT study from the PACS study list. As shown in FIG. 3, the medical images for the thoracic CT study may be displayed by the PACS workstation along with relevant prior images and scanned documents with the original order script, that is, the referral written by the ordering physician. In accordance with an example embodiment of the present invention, the PACS may also display a visual representation of the patient's body. The visual representation of the patient's body may be highlighted in order to indicate that the patient satisfies a respective risk profile, such as by highlighting the visual representation of the patient's body in red to indicate that the patient satisfies the cancer risk profile. In this example workflow, the visual representation of the patient's body includes visual indications of the findings related to the cancer risk profile. In the illustrated embodiment, the visual indications are icons, such as the two triangles on the visual representation of the patient's chest. Each visual representation may be provided in a manner that indicates the relevance or severity of the respective finding to the particular risk profile. In one embodiment, a radiologist or a group of users may predefine the relevance of a respective finding by assigning a weight to the respective finding. For example, the visual indications may be color-coded based upon relevance or severity and, in the illustrated embodiment, one icon on the visual representation of the patient's chest that is associated with a pathology report may be red so as to indicate particular relevance or severity, while the other icon that is associated with a radiology report may be yellow to indicate lesser relevance or severity. Similarly, a visual indication may be associated with the visual representation of the patient's leg with the visual indication associated with the patient's leg being associated with a dermatology report and indicated to be of lesser relevance or severity.

As shown in block 26 of FIG. 2, the apparatus 10 may also include means, such as the processing circuitry 12, the user interface 18 or the like, for providing information regarding a respective finding upon selection of the visual indication associated with the respective finding. With respect to the example of FIG. 3, a radiologist may select one or more of the visual indications in order to cause information associated with the respective finding to be provided, such as by being presented upon the display. For example, selection of the icon associated with the pathology report may provide information indicating that the pathology report relates to a biopsy performed six months ago that indicated the presence of a malignant tumor. Additionally, selection of the icon associated with the radiology report may cause information to be provided that indicates that a prior chest x-ray was obtained nine months ago. In one embodiment, a link to the prior chest x-ray may be provided in order to permit the radiologist to efficiently access the prior chest x-ray. Upon selection of the link, for example, the chest x-ray may be pulled up and displayed by the PACS workstation as a comparison study. For example, the chest x-ray may include annotations around a small nodule with the prior report associated with the prior chest x-ray including an impression of "possible pulmonary calcification, cannot rule out indications of small cell lung carcinoma-biopsy recommended." Further, selection of the icon associated with the dermatology report may provide information indicating that the patient has an open referral to a dermatologist to comment upon a large sun spot.

While the relevance or severity of a finding may be indicated by the color coding described above, the relevance or severity of a finding may be indicated in other manners, such as by the manner, e.g., the size, in which the information regarding a respective finding is presented. As shown in FIG. 3, for example, the information relating to the dermatology report is shown to be smaller than the information relating to the other reports since the dermatology report may be of lesser relevance since the sun spot has not grown since the original report in 2009 such that the likelihood that the sun spot is evidence of melanoma has been materially decreased.

By considering the information regarding the findings associated with the respective risk profile of the patient, the radiologist who is reviewing the medical images of the patient may interpret the medical images in a more informed manner. With respect to the foregoing example of FIG. 3, the radiologist may compare the annotated nodule from the prior chest x-ray to the newly acquired CT images that are presented by the PACS workstation and may report that the nodule does not appear to have grown in size or altered dimensions since the prior report. The radiologist of this example workflow may also observe a very minute mass in close proximity to the annotated nodule and may report that "given known smoking history and previous pathological findings, recommend biopsy of otherwise unremarkable mass". Thus, in light of the information associated with findings related to a cancer risk profile of the patient, the radiologist may recommend a biopsy of a very minute mass that is otherwise unremarkable and which may generally have not caused the radiologist to recommend any further action. As another example, a radiologist reviewing a chest x-ray who has been made aware of the patient's history with colon cancer through the findings associated with the patient's risk profile may flag any minor mass in the lungs as a potential pulmonary nodule, instead of dismissing the minor mass as calcification as might otherwise have happened in the absence of the clinical data.

Additionally, access to information regarding the findings related to the respective risk profile, such as access to the pathology report in the foregoing example workflow, may improve the efficiency with which a radiologist may review the medical images by eliminating any need for the radiologist to contact the ordering physician. Further, the information associated with findings related to a respective risk profile may permit a radiologist who is reviewing the medical images of the patient to quickly navigate through the relevant clinical data of the patient, such as prior examination report.

In one embodiment, the presentation of the visual representation of the patient's body with visual indications of one or more findings may be associated with a respective point in time. In addition, the apparatus 10 of this embodiment may also include means, such as the processing circuitry 12, the user interface 18 or the like, for receiving user input that identifies the point in time for which the visual representation of the patient's body with visual indications of one or more findings should be presented. In the embodiment illustrated in FIGS. 3 and 4, for example, a representation of a timeline may be provided with a mechanism, such as the slider in the illustrated embodiment, to permit a user to select a point in time. Based upon the selected point in time, the resulting presentation of the visual representation of the patient's body may include visual indications for only those findings that existed as of the selected point in time with the relevance or severity being indicated in a manner consistent with the relevance or severity of the respective finding at the selected point in time. For example, in 2013, FIG. 3 includes visual representations for three findings since all three findings were obtained prior to 2013 with the information associated with the dermatology report being indicated to be of lesser relevance or severity than the other reports since the sun spot has been determined not to have grown since its initial identification in 2009. In contrast, in 2010, FIG. 4 includes a visual representation of only a single finding, that is, the pathology report, since the other two reports were not generated until after 2010. Additionally, the information associated with the dermatology report is indicated to be of greater relevance or severity in FIG. 4 than in FIG. 3 since the linkage, if any, between the sun spot and melanoma had not yet been determined in 2010. By reviewing the visual representation of the patient's body with visual indications of one or more findings at different points in time, particularly in conjunction with a review of a plurality of medical images of the patient provides a useful and intuitive mechanism for a radiologist to obtain additional information regarding the patient and to quickly discern changes in the risk factors and the relevance of the findings over time, thereby further informing the radiologist's conclusions regarding the patient.

As described above, FIG. 2 illustrates a flowchart of a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a computing device, e.g., a PACS, and executed by a processing circuitry 12 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 12 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method comprising:
   identifying, with processing circuitry, one or more findings related to a respective risk profile of a patient based upon a review of clinical data associated with the patient, wherein one or more risk profiles are relevant to a respective type of medical image, and wherein identifying one or more findings related to a respective risk profile of the patient comprises tailoring review of the clinical data based upon the respective type of medical image so as to identify one or more findings related to a risk profile that is relevant to the respective type of medical image;
   concurrently presenting both one or more medical images of the patient and a visual representation of at least a portion of the patient's body, distinct from the one or more medical images, with respective visual indications of the one or more findings being associated with the visual representation of at least a portion of the patient's body; and providing information regarding a respective finding upon selection of the visual indication associated with the respective finding.

2. A method according to claim 1 wherein identifying one or more findings related to a respective risk profile comprises semantically analyzing data from an electronic medical record of the patient to identify the one or more findings.

3. A method according to claim 1 wherein concurrently presenting both one or more medical images of the patient and a visual representation of at least a portion of the patient's body comprises concurrently presenting both one or more medical images of the patient and the visual representation of at least a portion of the patient's body on the same display screen.

4. A method according to claim 1 wherein concurrently presenting both one or more medical images of the patient and a visual representation of at least a portion of the patient's body comprises highlighting the representation of at least a portion of the patient's body to indicate that the patient satisfies a respective risk profile.

5. A method according to claim 1 wherein concurrently presenting both one or more medical images of the patient and a visual representation of at least a portion of the patient's body comprises causing an indication of the relevance or severity of the one or more findings to be provided.

6. A method according to claim 1 wherein concurrently presenting both one or more medical images of the patient and a visual representation of at least a portion of the patient's body comprises concurrently presenting one or more prior images of the patient and an original order script.

7. An apparatus comprising processing circuitry configured to:
identify one or more findings related to a respective risk profile of a patient based upon a review of clinical data associated with the patient, wherein one or more risk profiles are relevant to a respective type of medical image, and wherein the processing circuitry is configured to identify one or more findings related to a respective risk profile of the patient by tailoring review of the clinical data based upon the respective type of medical image so as to identify one or more findings related to a risk profile that is relevant to the respective type of medical image;
concurrently present both one or more medical images of the patient and a visual representation of at least a portion of the patient's body, distinct from the one or more medical images, with respective visual indications of the one or more findings being associated with the visual representation of at least a portion of the patient's body; and
provide information regarding a respective finding upon selection of the visual indication associated with the respective finding.

8. An apparatus according to claim 7 wherein the processing circuitry is configured to identify one or more findings related to a respective risk profile by semantically analyzing data from an electronic medical record of the patient to identify the one or more findings.

9. An apparatus according to claim 7 wherein the processing circuitry is configured to concurrently present both one or more medical images of the patient and a visual representation of at least a portion of the patient's body by concurrently presenting both one or more medical images of the patient and the visual representation of at least a portion of the patient's body on the same display screen.

10. An apparatus according to claim 7 wherein the processing circuitry is configured to concurrently present both one or more medical images of the patient and a visual representation of at least a portion of the patient's body by highlighting the representation of at least a portion of the patient's body to indicate that the patient satisfies a respective risk profile.

11. An apparatus according to claim 7 wherein the processing circuitry is configured to concurrently present both one or more medical images of the patient and a visual representation of at least a portion of the patient's body by causing an indication of the relevance or severity of the one or more findings to be provided.

12. An apparatus according to claim 7 wherein the processing circuitry is configured to concurrently present both one or more medical images of the patient and a visual representation of at least a portion of the patient's body by concurrently presenting one or more prior images of the patient and an original order script.

13. A computer program product comprising at least one non-transitory computer-readable storage medium having computer-executable program code instructions stored therein, the computer-executable program code instructions comprising program code instructions configured to:
identify one or more findings related to a respective risk profile of a patient based upon a review of clinical data associated with the patient, wherein one or more risk profiles are relevant to a respective type of medical image, and wherein the program code instructions configured to identify one or more findings related to a respective risk profile of the patient comprise program code instructions configured to tailor review of the clinical data based upon the respective type of medical image so as to identify one or more findings related to a risk profile that is relevant to the respective type of medical image;
concurrently present both one or more medical images of the patient and a visual representation of at least a portion of the patient's body, distinct from the one or more medical images, with respective visual indications of the one or more findings being associated with the visual representation of at least a portion of the patient's body; and
provide information regarding a respective finding upon selection of the visual indication associated with the respective finding.

14. A computer program product according to claim 13 wherein the program code instructions configured to identify one or more findings related to a respective risk profile comprise program code instructions configured to semantically analyze data from an electronic medical record of the patient to identify the one or more findings.

15. A computer program product according to claim 13 wherein the program code instructions configured to concurrently present both one or more medical images of the patient and a visual representation of at least a portion of the patient's body comprise program code instructions configured to concurrently present both one or more medical images of the patient and the visual representation of at least a portion of the patient's body on the same display screen.

16. A computer program product according to claim 13 wherein the program code instructions configured to concurrently present both one or more medical images of the patient and a visual representation of at least a portion of the patient's body comprise program code instructions configured to highlight the representation of at least a portion of the patient's body to indicate that the patient satisfies a respective risk profile.

17. A computer program product according to claim 13 wherein the program code instructions configured to concurrently present both one or more medical images of the patient and a visual representation of at least a portion of the patient's body comprise program code instructions configured to cause an indication of the relevance or severity of the one or more findings to be provided.

* * * * *

UNITED STATES PATENT AND TRADEMARK OFFICE
CERTIFICATE OF CORRECTION

PATENT NO.         : 9,095,315 B2                                              Page 1 of 1
APPLICATION NO.    : 13/836666
DATED              : August 4, 2015
INVENTOR(S)        : Arazi It is certified that error appears in the above-identified patent and that said Letters Patent is hereby corrected as shown below:

<u>On the Title page, Item (54) and in the Specification, Column 1,</u>
Lines 1 - 3, in the title, "METHOD AND APPARATUS INTEGRATING CLINICAL DATA WITH THE REVIEW OF MEDICAL IMAGES" should read --METHOD AND APPARATUS FOR INTEGRATING CLINICAL DATA WITH THE REVIEW OF MEDICAL IMAGES--.

Signed and Sealed this
Fifteenth Day of March, 2016

Michelle K. Lee
*Director of the United States Patent and Trademark Office*